(12) United States Patent
Seguin et al.

(10) Patent No.: US 7,289,032 B2
(45) Date of Patent: Oct. 30, 2007

(54) INTELLIGENT FLAME SCANNER

(75) Inventors: Michel J. Seguin, Orleans (CA); James P. Sutton, South Windsor, CT (US); Rebecca L. Tobiasz, Suffield, CT (US); Matthew D. Odinotski, Pointe Claire (CA)

(73) Assignee: ALSTOM Technology Ltd (CH)

( * ) Notice: Subject to any disclaimer, the term of this patent is extended or adjusted under 35 U.S.C. 154(b) by 377 days.

(21) Appl. No.: 11/063,602

(22) Filed: Feb. 24, 2005

(65) Prior Publication Data

US 2006/0199123 A1    Sep. 7, 2006

(51) Int. Cl.
G06K 9/00    (2006.01)
G06K 9/34    (2006.01)
F23N 5/08    (2006.01)
G08B 17/12   (2006.01)

(52) U.S. Cl. ................. 340/578; 431/79; 382/164
(58) Field of Classification Search ........... 340/577, 340/578, 627–630; 382/164, 165, 170, 171; 431/75–79, 13
See application file for complete search history.

(56) References Cited

U.S. PATENT DOCUMENTS

| | | | |
|---|---|---|---|
| 4,220,857 A | 9/1980 | Bright | 250/339 |
| 4,913,647 A | 4/1990 | Bonne et al. | 431/12 |
| 5,625,342 A * | 4/1997 | Hall et al. | 340/578 |
| 5,850,182 A * | 12/1998 | Schuler | 340/578 |
| 6,045,353 A | 4/2000 | VonDrasek et al. | 432/79 |
| 6,111,511 A * | 8/2000 | Sivathanu et al. | 340/577 |
| 6,135,760 A | 10/2000 | Cusack et al. | 431/79 |
| 6,184,792 B1 * | 2/2001 | Privalov et al. | 340/578 |
| 6,356,199 B1 * | 3/2002 | Niziolek et al. | 340/579 |
| 6,680,671 B2 * | 1/2004 | Okamoto et al. | 340/578 |
| 7,002,478 B2 * | 2/2006 | Moore et al. | 340/577 |
| 2005/0130087 A1 * | 6/2005 | Chase et al. | 431/79 |
| 2006/0017578 A1 * | 1/2006 | Shubinsky et al. | 340/578 |

FOREIGN PATENT DOCUMENTS

DE    19746786    4/1999
EP    0616200     9/1994

* cited by examiner

Primary Examiner—Benjamin C. Lee
Assistant Examiner—Jennifer Mehmood
(74) Attorney, Agent, or Firm—Antonelli, Terry, Stout & Kraus, LLP

(57) ABSTRACT

Techniques for determining a characteristic of a flame are provided by the present invention. Provided are methods as well as devices. A flame is monitored across a contiguous spectral range to detect light emitted by the monitored flame. The contiguous spectral range is segmented into a plurality of discrete ranges, and detected light across each of the one or more of the plurality of discrete ranges is respectively processed to determine at least one characteristic of the flame.

20 Claims, 4 Drawing Sheets

INTELLIGENT FLAME SCANNER

FIELD OF THE INVENTION

The present invention is related to a flame scanner for monitoring flames produced by a fossil fuel fired combustion chamber, and more particularly to such a flame scanner that provides an indication of both presence and characteristics of a flame.

BACKGROUND OF THE INVENTION

A flame scanner monitors the combustion process in a fossil fuel fired combustion chamber to provide a signal indicating the presence or absence of a stable flame. With the presence of a stable flame it is safe to continue feeding fossil fuel into the combustion chamber of the steam generator. In the event that the flame becomes unstable, or the flame is lost completely (known as a flame out condition), the flame scanner provides a loss of flame signal. Based upon a loss of flame signal, fossil fuel delivery to the combustion chamber can be discontinued before an unsafe operating condition develops. In some systems, a human operator interrupts the fuel supply based upon the loss of flame signal; in other systems a burner management system (BMS) interrupts the fuel supply based upon the loss of flame signal.

Conventional flame scanners produce an electrical signal based upon a monitored flame. This resulting analog electrical signal is transmitted to processing electronics that are housed separately from the flame scanner, typically in an equipment rack located adjacent to a control room. The strength of the produced signal is typically proportional to the intensity of the monitored flame. If the signal strength falls below a lower set point, or raises above an upper set point, delivery of main fuel into the combustion chamber is interrupted. Set points are sometimes referred to as trip points.

The signal path from each flame scanner to the processing electronics is via a double-shielded cable, which typically includes five conductors. Because of the size of each double-shielded cable as well as the number of double-shielded cables, one being required for each flame scanner, a considerable amount of space is necessary for routing cable bundles to the processing electronics. Additionally, because of the type and number of cables required, high initial capital outlay costs are required. Accordingly, a need exists for a flame scanner having fewer and less expensive cabling requirements.

One type of flame scanner is an ultraviolet tube flame scanner which produces a pulsed electrical output whose pulse rate is proportional to the intensity of ultraviolet light, in the range of approximately 250 to 400 nanometers, emitted by a flame. These scanners are particularly suited for monitoring gas flames since the emission from gas flames can be primarily in the ultraviolet range, with only minimal visible light emissions. Ultraviolet flame scanners based on Geiger mueller tubes require extensive maintenance and have relatively limited operational lives as well as unsafe failure modes.

Another type of flame scanner is a photodiode flame scanner. Photodiode flame scanners are the most prevalent type of flame scanner in use today in industrial application. In these flame scanners, visible light, in the range of approximately 400 to 675 nanometers, is collected from inside a combustion chamber, transmitted through a fiber optic cable, and directed onto a single photodiode to produce an electrical signal utilized by the separate processing electronics. Photodiode flame scanners are well suited for monitoring oil and coal flames, as emissions from such flames are in the visible and near infrared ranges.

Flames produced by the burning of different types of fuels have different characteristics. For example, a flame produced by burning a first fuel (a first flame type) might produce one color light, i.e., light in one portion of the spectrum, while a flame produced by burning a second fuel (a second flame type) might produce another, different, color light, i.e., light in a different portion of the spectrum. Conventional flame scanners do not differentiate between, or even recognize, different colors. That is, conventional flame scanners 'see' in black-and-white.

However, one conventional flame scanner is known that can recognize an oil flame when oil flames and coal flames are present. However, this flame scanner cannot, at the same time, recognize the coal flame. Thus, this flame scanner is somewhat useful for monitoring oil flames, but limited in monitoring coal flames.

Many modern combustion chambers burn two types of fuels, such as a dual coal and oil burner system. Additionally, a gas- or oil-fired ignitor may be typically used as an ignition source for the main fuel(s). Thus, it is not uncommon for multiple types of flame scanners, one for each type of fuel, to be utilized together. It should be noted that the types of fuels are not limited to oil, coal, and natural gas. Other types of fuels whose flames are monitored include, but are not limited to, black liquor and waste gas fuels.

Utilizing multiple types of flame scanners results in higher initial capital outlays, as well as increased maintenance costs. If a single flame scanner could detect flames produced by multiple types of fuels, fewer flame scanners would be required, reducing both capital and maintenance costs. Accordingly, a need exists for a flame scanner that can detect flames produced by multiple types of fuels.

OBJECTS OF THE INVENTION

It is an object of the present invention to provide a flame scanner having reduced cabling requirements.

It is another object of the present invention to provide a flame scanner having reduced cabling requirements while maintaining suitable redundancy and integration to bus.

It is also an object of the present invention to provide a flame scanner capable of detecting flames produced by multiple types of fuels.

Another object of the present invention is to provide a flame scanner that is capable of differentiating between multiple monitored flames.

Still another object of the present invention is to provide a flame scanner that is capable of simultaneous monitoring of multiple flame types.

The above-stated objects, as well as other objects, features, and advantages, of the present invention will become readily apparent from the following detailed description which is to be read in conjunction with the appended drawings.

SUMMARY OF THE INVENTION

A method and a flame scanner for determining a characteristic of a flame are provided herein. The determined characteristic could be any type of characteristic associated with a flame, including, but not limited to, flame presence, flame quality, flame type, and an air/fuel mixture ratio. The flame scanner includes a flame sensor, a splitter, and a processor. The flame sensor, splitter, and processor operate together to implement the method described herein. Also, in some aspects of the present invention, the flame scanner includes a memory, and in others the flame scanner includes a display.

In accordance with the method, a flame is monitored across a contiguous spectral range to detect light emitted by the flame. That is, all light emitted by the flame in that continuous, unbroken spectral range is detected. The contiguous spectral range is segmented into multiple discrete ranges. Detected light in each of at least one discrete range is respectively processed to determine at least one characteristic of the flame. Thus, detected light in only one or more certain ranges is processed to determine a characteristic, or characteristics.

In one aspect of the present invention, the monitored contiguous spectral range is 350 to 1100 nanometers. Thus, light that falls within the range of 350 to 1100 nanometers is detected. In another aspect, the plurality of discrete ranges is at least seven ranges.

According to another aspect of the present invention, at least one flame signature is stored. Each flame signature is associated with burning a particular type of fuel. Thus, a first flame signature might be associated with burning one type of oil, while a second flame signature could be associated with burning natural gas. A flame signature consists of known data associated with burning a particular type fuel. In this aspect, the processing to determine the at least one characteristic includes processing the detected light, across the one or more discrete ranges, along with one stored flame signature. Thus, the one or more characteristic is determined based both upon the detected light and a stored flame signature.

In a further aspect, each stored flame signature includes at least one of multiple types of information associated with burning a type of fuel. The information is at least one of DC intensity data, flicker intensity data, flicker frequency data, and spectral shape data.

In another further aspect, two flames are monitored at the same time. The first flame is associated with a first type fuel, and the second flame is associated with a second type fuel different than the first type fuel. Detected light emitted by the second flame across each of one or more of the multiple discrete ranges is respectively processed with another stored flame signature to determine at least one characteristic of the second flame. The other stored flame signature is different than the flame signature processed in determining the characteristic of the first flame. In this further aspect, the one or more discrete ranges associated with determining the one or more characteristics of the first flame could be the same as, or different than, the one or more discrete ranges associated with determining the one or more characteristics of the second flame.

According to an even further aspect, at least one of the plurality of ranges considered in determining the at least one characteristic of the first flame is not considered in determining the at least one characteristic of the second flame.

In another aspect of the present invention, the monitoring, segmenting, and processing are performed by a first one of a plurality of flame scanners. Information associated with the determination is transmitted from the first flame scanner to a remote location. This information is transmitted to the remote location via at least another one of the plurality of flame scanners. That is, the multiple flame scanners are serially linked to the remote location. The remote location, in this aspect, could be any location.

In still another aspect, the monitoring, segmenting, and processing are performed by a flame scanner, and information associated with the determination is displayed on the flame scanner. This information could be the determination itself, or information ancillary and associated with the determination. For example, the displayed information could be the spectral shape of the monitored flame.

BRIEF DESCRIPTION OF THE DRAWINGS

In order to facilitate a fuller understanding of the present invention, reference is now made to the appended drawings. These drawings should not be construed as limiting the present invention, but are intended to be exemplary only.

DETAILED DESCRIPTION OF A PREFERRED EMBODIMENT

Figure 1:
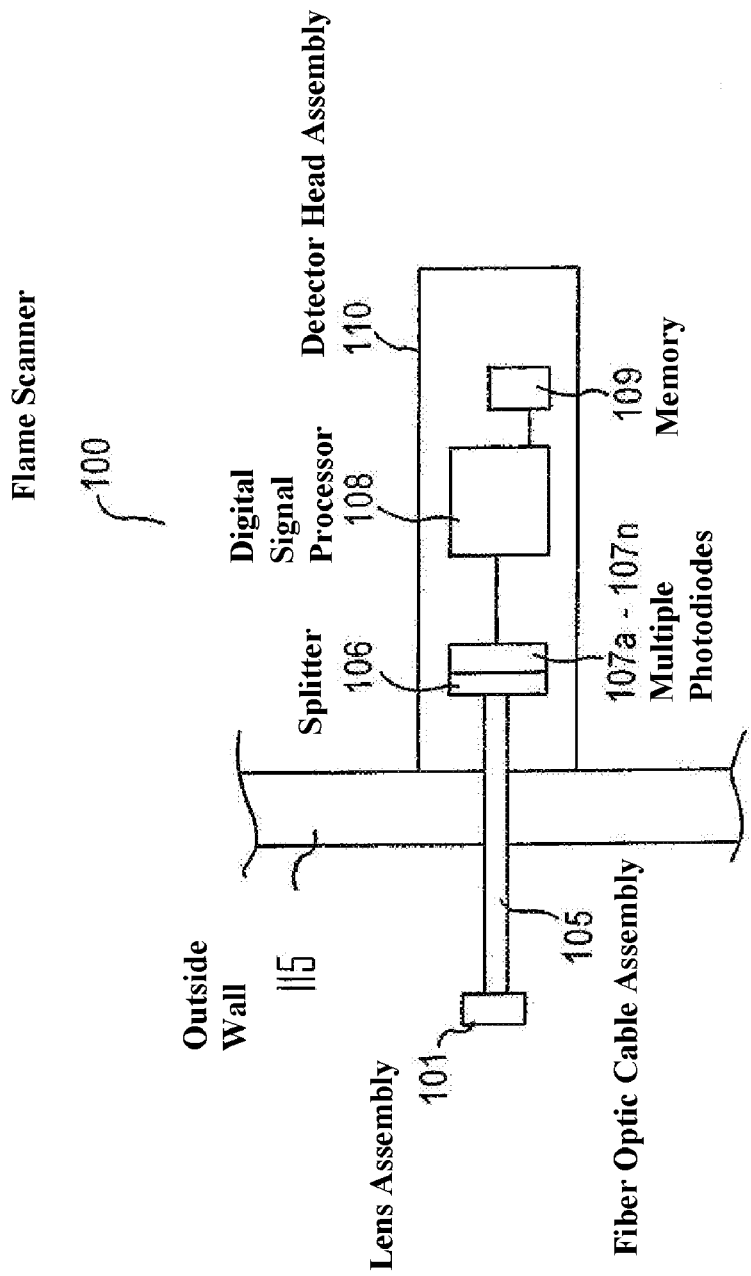
FIG. 1 is a simplified depiction of a flame scanner in accordance with the present invention.

With reference to the Figures, and particularly FIG. 1, included in a flame scanner 100 of the present invention are a lens assembly 101, a fiber optic cable assembly 105, and a detector head assembly 110. The detector head assembly 110 mounts to an outside wall 115 of a combustion chamber, while the lens assembly 101 is positioned inside the combustion chamber, with the fiber optic cable assembly 105 connecting the detector head assembly 110 and the lens assembly 101 through the outside wall 115. Preferably, all metal components of the lens assembly 101 and the fiber optic cable assembly 105 that are subjected to high heat are constructed of type 304 stainless steel. Flame scanner 100 may be, as desired, utilized in either tangential fired (T-fired) or wall-fired boilers, as well as used with any, or all of, coal-, oil-, gas-, and/or other fuel-fired burners. The detector head assembly 110 preferably is configured such that cooling and/or purge air may be connected, as desired. However, preferably the temperature rating of the lens assembly 101 and fiber optic cable is 900 degrees F., thus cooling air is not required. As desired, purge air may be utilized. Preferred purge air flow is 4-10 SCFM for low pressure air, such as that from a low pressure blower (10" wc), or 3-5 SCFM for compressed air. The detector head assembly 110 is cast aluminum, though other materials may be utilized, and includes pins (not shown) for mounting the detector head assembly 110 to the outside wall 115.

The lens assembly 101 includes a replaceable quartz lens. The fiber optic cable assembly 105 includes a fiber optic cable 103 that is preferably of a ⅛" diameter and made of blue enhanced borosilicate fiber optic cable. Use of a blue enhanced borosilicate fiber optic cable provides a cleaner signal path, improving light transmission as compared to other type fiber optic cables. The fiber optic cable 103 transmits light collected by the quartz lens to a splitter 106 located inside the detector head assembly 110. Quartz or other cables may be utilized, as desired.

The splitter 106 directs the collected light onto each of multiple photodiodes 107a-107n. Preferably, six photodiodes are utilized, however, fewer or more photodiodes could be utilized, as desired. Each photodiode 107a-107n converts light energy into an electrical signal. Each electrical signal is then sent to an onboard digital signal processor 108.

Use of an onboard digital signal processor 108 replaces the separate and remote processing electronics of conventional flame scanners. The digital signal processor 108 preferably samples at a rate of 2000 Hz to perform frequency analysis of between 10 to 200 Hz. Additionally, the digital signal processor 108 is preferably of a 16-bit design and operates at 40 MIPS, enabling real time frequency analysis. The electronics preferably include automatic gain control to allow a minimum of 18 bit analog to digital conversion.

The output from each of the multiple photodiodes 107a-107n represents flame intensity in a unique spectral range, from infra-red to ultraviolet frequencies. This provides a flame scanner having better flame discrimination, improved ability to distinguish one burner from another (between support fuel flame and other burner flames), and improved ability to discriminate the type of fuel being burned.

Taken together, these unique spectral ranges form a contiguous spectral range, including ultraviolet, visible, and infrared light. Preferably the contiguous spectral range is from 300 to 1100 nanometers. However, as desired, a wider or a narrower contiguous spectral range could be formed. The output from each photodiode 107a-107n is proportional to the intensity of the captured light in the respective unique spectral range.

The digital signal processor 108 communicates with a memory 109. As desired, the digital signal processor 108 and the memory 109 may be combined into a single unit. Stored in the memory 109 is at least one flame signature. Each stored flame signature represents a flame produced from burning a different type of fuel, such as natural gas, oil, and/or one or more types of coal.

Raw flame signature data is obtained by recording the DC voltage output from each of the multiple photodiodes 107a-107n over a finite time period, such as five minutes, resulting from the monitoring, with the flame scanner 100, of a flame known to be stable. This is known as auto-tuning. Alternatively, raw flame signature data may be gathered utilizing devices other than the flame scanner 100. In such a case, the raw flame signature data nonetheless corresponds to the specific spectral range associated with each of the multiple photodiodes 107a-107n. Preferably, the flame scanner memory 109 stores flame signatures for flames of each type of fuel burned in a combustion chamber monitored by the flame scanner 100. That is, a memory 109 of one flame scanner 100 can store a set of one or more flame signatures, while a memory 109 of another flame scanner 100 can store a different set of one or more flame signatures.

Figure 2:
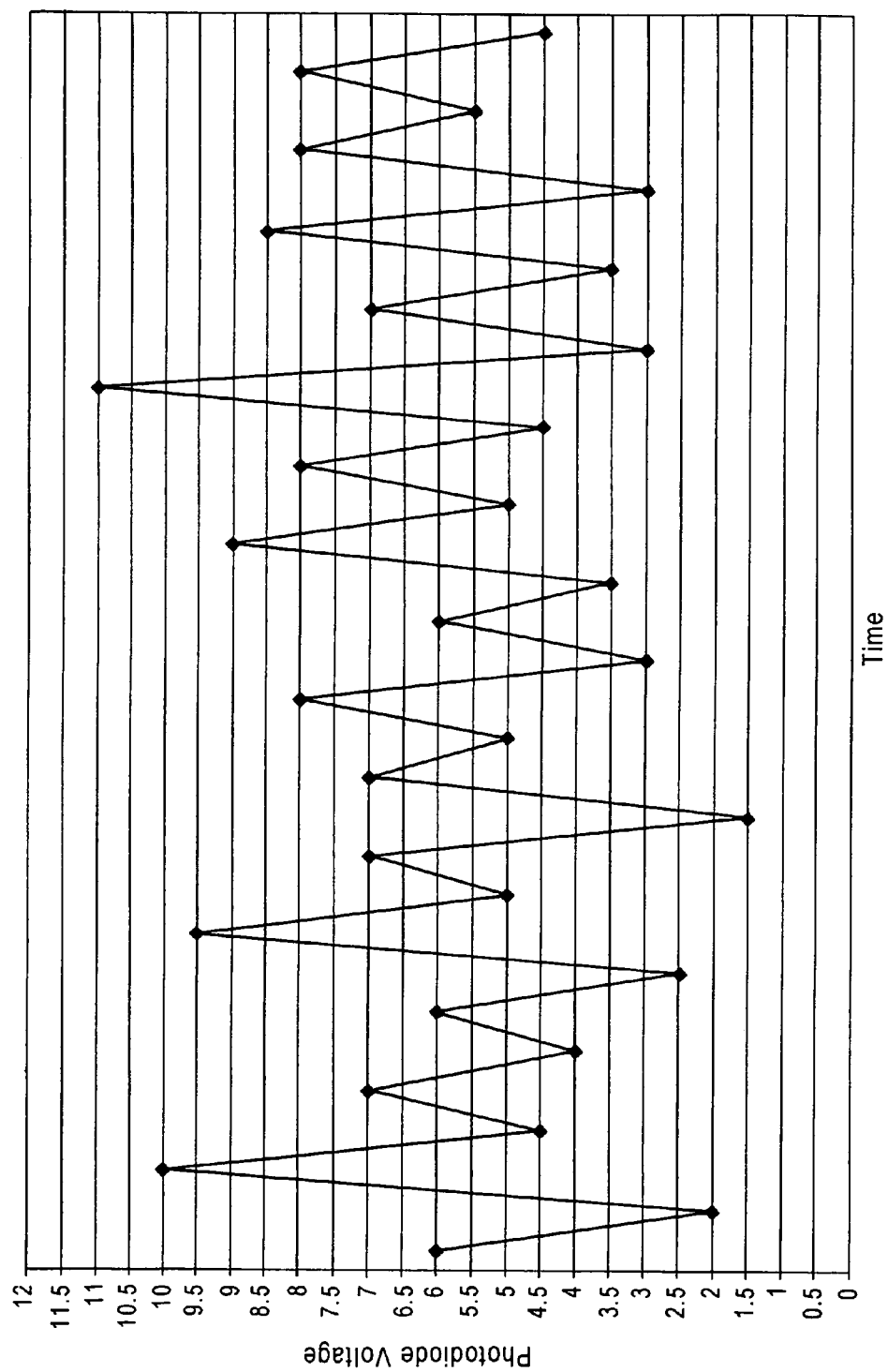
FIG. 2 is a graphical depiction of refined flame signature data stored by the flame scanner of FIG. 1.

FIG. 2 is a simplified graphical depiction of stored refined flame signature data for a single one of the multiple photodiodes 107a-107n. It should be understood that refined flame signature data for each one of the multiple photodiodes 107a-107n is stored in the memory 109. Refined flame signature data is based upon raw flame signature data. That is, raw flame signature data is converted into and stored as refined flame signature data by the digital signal processor 108.

A first type of refined flame signature data is known as DC intensity data. DC intensity data is closely related to the raw flame signature data. DC intensity data includes the maximum raw DC voltage recorded, the minimum raw DC voltage recorded, and an average raw DC voltage recorded, for each of the multiple photodiodes 107a-107n. For example, based upon the exemplary raw flame signature date of FIG. 2, the maximum raw DC voltage is 11, the minimum raw DC voltage is 1.5, and the average raw DC voltage is 6.

A second type of refined flame signature data is known as flicker intensity data and is a measure of the amplitude of each recorded peak of the raw flame signature data as compared to the recorded trough preceding that peak, for each of the multiple photodiodes 107a-107n. Flicker intensity data includes the maximum amplitude, the minimum amplitude, and average amplitude, for each of the multiple photodiodes 107a-107n.

A third type of refined flame signature data is known as flicker frequency data and is a measure of the number of peaks of the raw flame signature data within a given timeframe for each of the multiple photodiodes 107a-107n. Flicker frequency data includes the maximum flicker frequency, the minimum flicker frequency, and an average flicker frequency for each of the multiple photodiodes 107a-107n.

Figure 3:
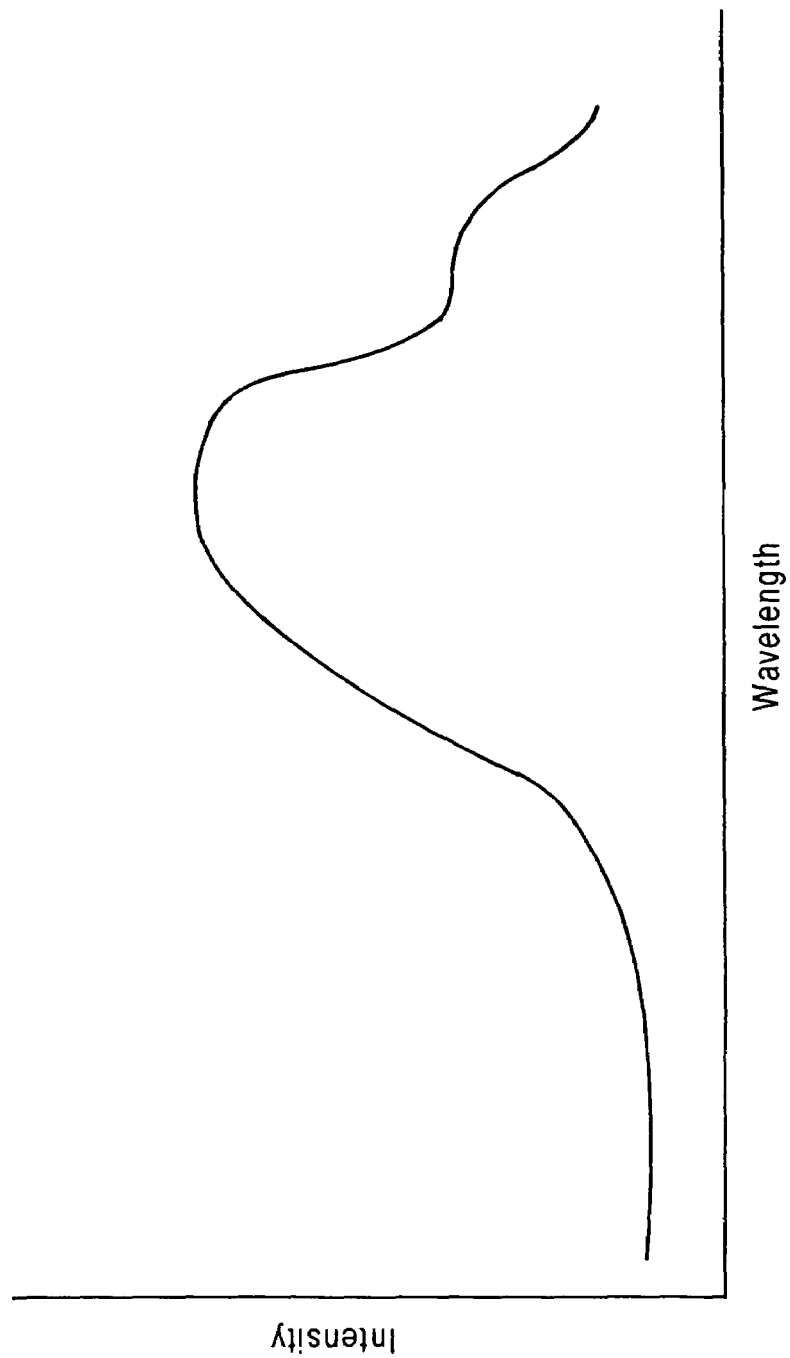
FIG. 3 is a graphical depiction of spectral shape data for a flame stored by the flame scanner of FIG. 1.

A fourth type of refined flame signature data is known as spectral shape data. This data, which is a combination of recorded raw data from each of the multiple photodiodes 107a-107n, reflects where on the spectrum a monitored flame produces light. FIG. 3 is a simplified graphical depiction of spectral shape data for a single monitored flame.

In operation, the signal processor 108 continually analyses the signals output from the multiple photodiodes 107a-107n in view of the stored flame signature data. Based upon this analysis, the flame scanner 100 reliably and accurately not only detects loss of flame, but also provides other information associated with monitored flames and the operation of the flame scanner 100 itself, as will be described below.

Loss of flame may be detected, as desired, based upon any one of, or any combination of, the different types of stored flame signature data. That is, loss of flame may be detected based upon DC intensity data, flicker intensity data, flicker frequency data and/or spectral shape data. Further, loss of flame may be detected, as desired, based upon stored flame signature data associated with any one of, or any combination of, the multiple photodiodes 107a-107n.

If the signal output from one or more photodiodes 107a-107n falls below one or more stored minimum value and/or stored average value, a trip signal is transmitted to a human operator and/or BMS controlling the monitored combustion chamber. Also, if the signal output from one or more photodiodes 107a-107n is greater than one or more stored maximum value, a trip signal is transmitted to the operator and/or BMS. Based upon receipt of such a signal, the operator and/or BMS may then take appropriate action, such as discontinuing supply of fuel to the combustion chamber. Thus, the stored minimums, maximums, and averages serve as set points for tripping fuel supply to the combustion chamber.

Because flames produced from the burning of different type fuels have different flame signatures, the signal processor 108 is programmable to generate trip signals based upon those flame signature characteristics known to be most closely associated with the flame being monitored. As introduced above, one type flame might produce light in one spectral range, while another type flame might produce light in another spectral range. Additionally, different type flames are more closely associated with different ones of DC intensity, flicker intensity, and flicker frequency. For example, for one type flame, flicker frequency might be the most reliable indicator of a stable flame. Thus, as desired, the signal processor 108 can be programmed to analyze only those signals associated with the spectral range of the monitored flame, i.e., only the signal output from certain of the multiple photodiodes 107a-107n, in view of one or more of the stored flame signature data, i.e., one or more of DC intensity data, flicker intensity data, and/or flicker frequency data.

If the signal processor 108 is programmed to analyze multiple signals in view of one or more ones of the stored flame signature data, the programming, as desired, can result in transmission of a trip signal if any one signal violates any single trip point. Alternatively, the programming, as desired, can result in transmission of a trip signal only if a certain combination of different trip points are violated, or only if a certain number of different trip points are violated.

The stored flame signature data may be modified, as desired. A modification can include a complete replacement of flame signature data by recording new raw flame signature data with the flame scanner 100 and the digital signal processor 108 producing new refined flame signature data based upon the new raw data. Also, modification can be made to individual pieces of stored flame signature data. For example, stored minimum DC intensity voltage for one of the multiple photodiodes 107a-107n, determined by the digital signal processor 108, may be changed. User interfaces for modifying stored data, as well as other purposes, will be discussed further below.

The flame scanner 100 also determines flame quality based upon DC voltage data. Flame quality information is useful for operators and repair technicians. That is, degradation of flame quality is beneficially the basis for performing service on the flame scanner 100, such as cleaning or replacing the lens assembly 101 and/or the quartz lens. Flame quality is determined by the processor 108 based upon the stored average DC intensity data, the stored minimum DC intensity data, and the monitored DC intensity. The stored average DC intensity data is equal to a flame quality of 100%, and the stored minimum DC intensity data is equal to a flame quality of 0%. Thus, as the monitored DC intensity moves closer to the stored minimum DC intensity, flame quality decreases.

The digital signal processor 108 is programmed to generate a service warning whenever the monitored DC intensity falls below a certain percent, i.e., comes within a certain distance from 0%. Alternatively, or perhaps additionally, the digital signal processor 108 may be programmed to generate a service warning whenever the monitored DC intensity begins to trend downward, perhaps at a certain rate. The memory 109 stores the certain percent and/or the certain rate. A generated service warning is preferably transmitted to the control room, or perhaps to a remote location.

In addition to transmitting trip signals based upon violation of one or more of DC intensity data, flicker intensity data, and/or flicker frequency data, the digital signal processor 108 may be programmed, as desired, to transmit a trip signal based upon the spectral shape of the monitored flame. Thus, when the spectral shape of the monitored flame does not correspond to the stored spectral shape, a trip signal may be transmitted. Correspondence may be, as desired, based upon a percentage deviation of the monitored spectral shape to that of the stored spectral shape. The deviation may be either or both of the amplitude of the monitored spectral shape and the distribution of the monitored flame across the spectrum. Also as desired, monitored spectral shape data may be combined with one or more of the other monitored flame signature data to generate a trip signal. Similar to the discussion above, if the digital signal processor 108 is programmed to analyze multiple signals in view of one or more ones of the stored flame signature data and the spectral shape of the monitored flame, the programming can, as desired, result in transmission of a trip signal if any one signal violates any one single trip point or if the monitored spectral shape deviates from the stored spectral shape. Alternatively, the programming can, as desired, result in transmission of a trip signal only if a certain combination of different trip points and/or the spectral shape are violated, or only if a certain number of the trips are violated.

Figure 4:
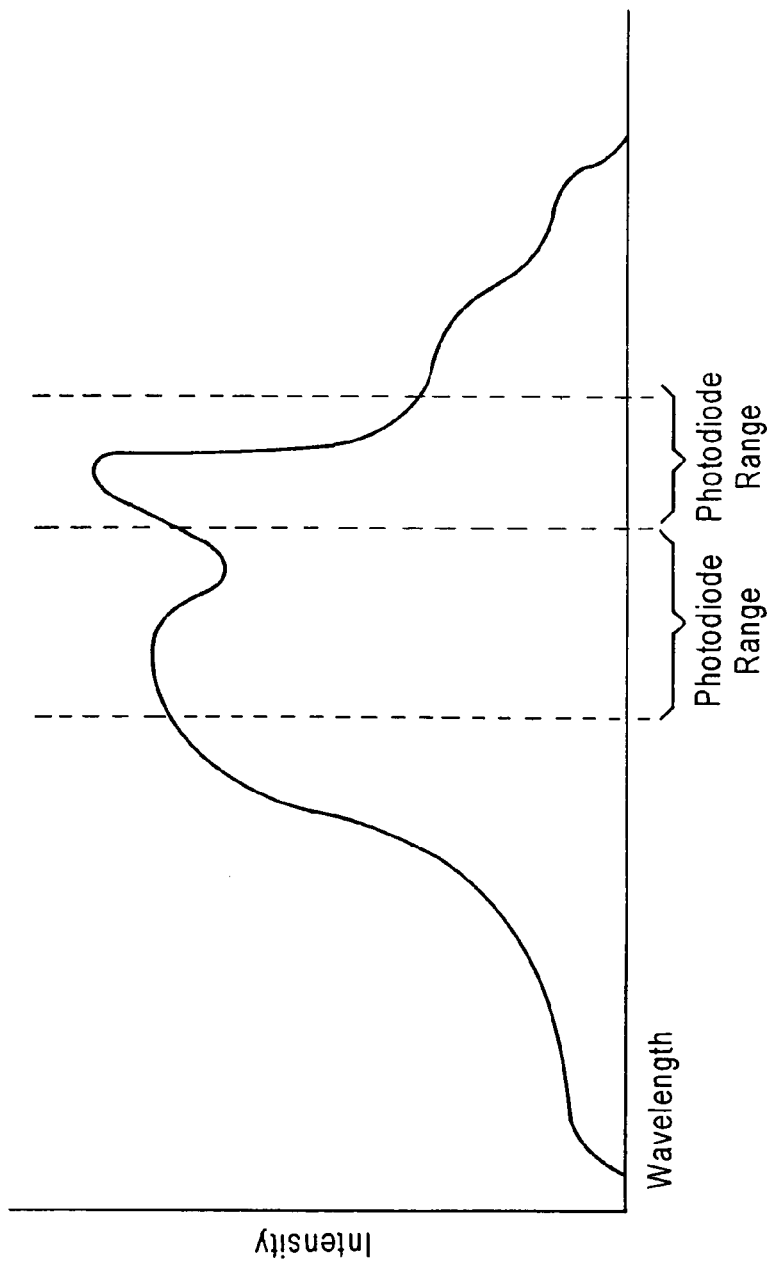
FIG. 4 is an exemplary depiction of photodiode wavelength sensitivity of the flame scanner of FIG. 1 in accordance with certain aspects of the present invention.

The stored spectral shape data is especially useful in discriminating between different types of flames in a single combustion chamber, thus reducing the number of scanners required. Introduced above, each type of flames produces light in a certain portion of the spectrum. Discussed above, the output from each photodiode 107a-107n is associated with a portion of the spectrum. It has been found that a ratio of relative peaks between certain ones of these outputs is a reliable indicator of a particular type of flame. For example, with reference to FIG. 4, a 1.2 ratio between a relative peak in a first portion of the spectrum (associated with one photodiode) and a relative peak in a second portion of the spectrum (associated with another photodiode) might be associated with a first type fuel. Thus, in this example, the relative peak in the second portion of the spectrum will always be 1.2 times higher than the relative peak in the first portion of the spectrum for this first type fuel.

These ratios have been proven to be reliable indicators of a flame type no matter how bright or how dim a flame is. The memory 109 stores ratios and the associated spectral portions for coal flames, oil flames, and gas flames. Based upon the monitored spectral data, a flame type can be determined and differentiated from other flame types being monitored at the same time by comparing the monitored spectrum to the stored ratio/spectral portion information. Thus, the inventive flame scanner disclosed herein can monitor, and provide a positive indication of presence of, a coal flame at the same time as monitoring a gas flame. Of course, other flame type combinations can also be monitored at the same time to provide an indication of flame presence by flame type.

The spectral data is also beneficially used to monitor the fuel/air mixture in the combustion chamber to control NOx emissions. Introduced above, the flame scanner 100 compares the spectral shape of a monitored flame to an expected spectral shape stored in the memory 109. Whenever the monitored flame does not have the expected spectral shape, the digital signal processor 108 analyses the monitored shape to determine if the fuel/air mixture ratio is correct. For example, too much yellow flame in a gas flame indicates the presence of an inappropriate amount of air in the mixture. The digital signal processor 108, in this example, would send a control signal directly to a burner management system to appropriately adjust the air in the mixture. Of course, such a corrective signal could alternatively be sent to the control room for operator use.

Outputs from the flame scanner 100 can be transmitted in various ways. Communication can be either by wiring to simple relays inside the flame scanner or through a sophisticated interface module of the digital signal processor 108. When by relays, the only information transmitted is generated trip signals.

However, when utilizing the interface module, all information produced by the digital signal processor 108 can be communicated to the control room, and as desired, remote locations. These communications can be, as desired, by Device Net, Industrial Ethernet, MODBUS, or RS-232 communication protocols.

Especially beneficial, multiple ones of flame scanner 100 may be linked serially by a single cable to the control room, thus reducing cabling requirements by 75% compared to current flame scanner installations. Thus, the outputs of multiple ones of flame scanner 100 may be marshaled together and transmitted via the same cable, while still maintaining redundancy required for safety.

As an example, a typical boiler includes four flame scanners (one per corner) on each of multiple levels. Thus, a four level boiler would have sixteen flame scanners. As described earlier, conventionally each of the sixteen flame scanners would be individually connected to the control room. That is, at least 16 cables would run to the control room. With the present invention, in this example, the number of cables is reduced to four, while still providing necessary redundancy. This is because, in this example, each of the four flame scanners 100 located on the same corner is serially connected to one another by a single cable that runs to the control room. This same arrangement is repeated for the remaining three corners. Even if two cables are severed or fail for some other reason, two flame scanners 100 on each level are still able to transmit information.

Any information that available for transmission by the flame scanner 100 is also is available via a user interface located on the back of the flame scanner 100. At the rear of the flame scanner 100 is a LED bargraph display which can be set to indicate flame quality, intensity, or any other parameters monitored, calculated, and/or determined by the flame scanner 100. Additionally, the LED graph can be set to display the entire measured spectrum in real time, or only a portion of the measured spectrum.

All operational parameters can also be set from this user interface, in addition to via the network connection. These parameters include modifications to all stored information discussed above, including the set points and the flame signature data, whether raw or refined. Access to these operational parameters is controlled by password. Access to the user interface via the network connection can be done in the control room via a dedicated interface. Beneficially, network access to the user interface can also be made via a PC connected directly to the flame scanner 100, as well as via a PC in the control room.

The present invention is not to be limited in scope by the specific embodiments described herein. Indeed, various modifications of the present invention in addition to those described herein will be apparent to those of skill in the art from the foregoing description and accompanying drawings. Thus, such modifications are intended to fall within the scope of the appended claims.

We claim:

1. A method for determining a characteristic of a flame, comprising:
    monitoring a flame to detect light emitted by the flame in each of a plurality of discrete spectral ranges forming a contiguous spectral range;
    generating a respective voltage corresponding to an intensity of the detected light in each of the discrete spectral ranges;
    recording raw flame signature data for the monitored flame representing the generated voltages for each of the discrete spectral ranges over a period of time;
    converting the recorded raw flame signature data into refined flame signature data; and
    determining at least one characteristic of the flame based on the refined flame signature data;
    wherein the refined flame signature data includes one of (i) DC intensity data, for each of the discrete spectral ranges, representing a maximum recorded raw DC voltage, a minimum recorded raw DC voltage and an average recorded raw DC voltage, (ii) flicker intensity data, for each of the discrete spectral ranges, representing a maximum difference between amplitudes of each peak and of the immediately preceding trough in the recorded raw DC voltage, a minimum difference between amplitudes of each peak and of the immediately preceding trough in the recorded raw DC voltage and an average difference between amplitudes of each peak and of the immediately preceding trough in the recorded raw DC voltage, and (iii) flicker frequency data, for each of the discrete spectral ranges, representing a maximum frequency of flickers in the recorded raw DC voltage, a minimum frequency of flickers in the recorded raw DC voltage and an average frequency of flickers in the recorded raw DC voltage.

2. The method of claim 1, wherein the monitored contiguous spectral range is 350 to 1100 nanometers.

3. The method of claim 2, wherein the plurality of discrete ranges is seven discrete ranges.

4. The method of claim 1,
    wherein the at least one characteristic of the flame is determined by comparing the refined flame signature data with first predetermined refined flame signature data associated with burning a first type of fuel.

5. The method of claim 4, wherein the refined flame signature data also includes spectral shape data representing a spectrum of the detected light corresponding to a combination of the generated voltages represented by the recorded raw flame signature data for the monitored flame, and the first predetermined refined flame signature data includes first predetermined spectral shape data representing a spectrum of detected light associated with burning the first type of fuel, and further comprising:
    determining that the monitored flame is associated with burning the first type of fuel by comparing the spectral shape data with the first predetermined spectral shape data.

6. The method of claim 5, wherein the flame is a first flame, and further comprising:
    monitoring a second flame across the contiguous spectral range to detect light emitted by the second flame in each of the plurality of discrete spectral ranges while monitoring the first flame;
    generating another respective voltage corresponding to an intensity of the detected light from the monitored second flame in each of the discrete spectral ranges;
    recording other raw flame signature data for the monitored second flame representing the generated other voltages for each of the discrete spectral ranges over a period of time;
    converting the recorded other raw flame signature data into other refined flame signature data including other spectral shape data representing a spectrum of the detected light from the monitored second flame corresponding to a combination of the other voltages represented by the recorded other raw flame signature data; and
    determining that the monitored second flame is associated with burning the second type of fuel by comparing the other spectral shape data with second predetermined spectral shape data representing a spectrum of detected light associated with burning the second type of fuel.

7. The method of claim 6, wherein:
    the spectral shape data for the monitored first flame corresponds to the generated voltages associated with the detected light in a first of the plurality of discrete spectral ranges; and
    the other spectral shape data for the monitored second flame does not correspond to the generated voltages associated with the detected light in the first of the plurality of discrete spectral ranges.

8. The method of claim 5, wherein the comparison of the spectral shape data with the first predetermined spectral shape data includes:
    computing a first ratio between relative peaks of the spectral shape data associated with different of the plurality of discrete spectral ranges and a second ratio between relative peaks of the first predetermined spectral shape data associated with the different discrete spectral ranges; and comparing the first ratio with the second ratio to determine that the monitored flame is associated with burning the first type of fuel.

9. The method of claim 1, wherein the monitoring, generating, recording and converting are performed by a first of a plurality of flame scanners, and further comprising:
transmitting information indicative of the at least one determination from the first flame scanner to a remote location via a second of the plurality of flame scanners.

10. The method of claim 1, wherein the monitoring, generating, recording and converting are performed by a flame scanner, and further comprising:
displaying information indicative of the at least one determination at the flame scanner.

11. A flame scanner for monitoring a flame, comprising:
a flame sensor configured to monitor a flame to detect light emitted by the flame in each of a plurality of discrete spectral ranges forming a contiguous spectral range and to generate a respective voltage corresponding to an intensity of the detected light in each of the discrete spectral ranges;
memory configured to record raw flame signature data for the monitored flame representing the generated voltages for each of the discrete spectral ranges over a period of time; and
a processor configured to convert the recorded raw flame signature data into refined flame signature data, and to determine at least one characteristic of the flame based on the refined flame signature data;
wherein the refined flame signature data includes one of (i) DC intensity data, for each of the discrete spectral ranges, representing a maximum recorded raw DC voltage, a minimum recorded raw DC voltage and an average recorded raw DC voltage, (ii) flicker intensity data, for each of the discrete spectral ranges, representing a maximum difference between amplitudes of each peak and of the immediately preceding trough in the recorded raw DC voltage, a minimum difference between amplitudes of each peak and of the immediately preceding trough in the recorded raw DC voltage and an average difference between amplitudes of each peak and of the immediately preceding trough in the recorded raw DC voltage, and (iii) flicker frequency data, for each of the discrete spectral ranges, representing a maximum frequency of flickers in the recorded raw DC voltage, a minimum frequency of flickers in the recorded raw DC voltage and an average frequency of flickers in the recorded raw DC voltage.

12. The flame scanner of claim 11, wherein the monitored contiguous spectral range is 350 to 1100 nanometers.

13. The flame scanner of claim 12, wherein the plurality of discrete ranges is seven discrete ranges.

14. The flame scanner of claim 11, wherein:
the memory is further configured to store first predetermined refined flame signature data, the stored first predetermined refined flame signature being associated with burning a first type of fuel;
the processor is further configured to determine the at least one characteristic of the flame by comparing the refined flame signature data with the stored first predetermined refined flame signature data.

15. The flame scanner of claim 14, wherein:
the refined flame signature data also includes spectral shape data representing a spectrum of the detected light corresponding to a combination of the generated voltages represented by the recorded raw flame signature data;
the stored first predetermined refined flame signature data includes first predetermined spectral shape data representing a spectrum of detected light associated with burning the first type of fuel; and
the processor is further configured to determine that the monitored flame is associated with burning the first type of fuel by comparing the spectral shape data with the first predetermined spectral shape data.

16. The flame scanner of claim 15, wherein:
the flame is a first flame;
the flame sensor is further configured to monitor a second flame across the contiguous spectral range to detect light emitted by the second flame in each of the plurality of discrete spectral ranges while monitoring the first flame, and to generate another respective voltage corresponding to an intensity of the detected light from the monitored second flame in each of the discrete spectral ranges;
the memory is further configured to record other raw flame signature data for the monitored second flame representing the generated other voltages for each of the discrete spectral ranges over a period of time, and to store second predetermined refined flame signature data including second predetermined spectral shape data representing a spectrum of detected light associated with burning the second type of fuel; and
the processor is further configured to convert the recorded other raw flame signature data into other refined flame signature data including other spectral shape data representing a spectrum of the detected light from the monitored second flame corresponding to a combination of the recorded other voltages, and to determine at that the monitored second flame is associated with burning the second type of fuel by comparing the other spectral shape data with the second predetermined spectral shape data.

17. The flame scanner of claim 16, wherein:
the spectral shape data for the monitored first flame corresponds to the generated voltages associated with the detected light in a first of the plurality of discrete spectral ranges; and
the other spectral shape data for the monitored second flame does not correspond to the generated voltages associated with the detected light in the first discrete spectral range.

18. The flame scanner of claim 15, wherein the processor is further configured to compare the spectral shape data with the first predetermined spectral shape data by computing a first ratio between relative peaks of the spectral shape data associated with different of the plurality of discrete spectral ranges and a second ratio between relative peaks of the first predetermined spectral shape data associated with the different discrete spectral ranges, and comparing the first ratio with the second ratio to determine that the monitored flame is associated with burning the first type of fuel.

19. The flame scanner of claim 11, further comprising:
a housing; and
a display configured to present information indicative of the at least one determination;
wherein the flame sensor, the memory, and the processor are disposed within the housing; and
wherein the display is disposed at the housing.

20. The flame scanner of claim 11, wherein:
the flame scanner is one of a plurality of flame scanners;
the processor is further configured to transmit information indicative of the at least one determination to a remote location
via at least another one of the plurality of flame scanners.

* * * * *